(12) United States Patent
Rahimi (10) Patent No.: US 9,119,693 B2
(45) Date of Patent: Sep. 1, 2015

(54) DYNAMIC BRACKET SYSTEM

(76) Inventor: Hessam Rahimi, Dallas, TX (US)

( * ) Notice: Subject to any disclaimer, the term of this patent is extended or adjusted under 35 U.S.C. 154(b) by 0 days.

(21) Appl. No.: 13/598,931

(22) Filed: Aug. 30, 2012

(65) Prior Publication Data

US 2014/0065567 A1     Mar. 6, 2014

(51) Int. Cl.
  A61C 3/00      (2006.01)
  A61C 7/14      (2006.01)
  A61C 7/16      (2006.01)
  A61C 7/22      (2006.01)

(52) U.S. Cl.
  CPC . *A61C 7/146* (2013.01); *A61C 7/14* (2013.01); *A61C 7/16* (2013.01); *A61C 7/22* (2013.01); *A61C 7/141* (2013.01)

(58) Field of Classification Search
  CPC .............. A61C 7/14; A61C 7/16; A61C 7/18; A61C 7/141; A61C 7/143; A61C 7/145; A61C 7/146; A61C 7/148
  USPC ........................................................ 433/8–24
  See application file for complete search history.

(56) References Cited

U.S. PATENT DOCUMENTS

| | | | | |
|---|---|---|---|---|
| 3,421,221 A | * | 1/1969 | Silverman et al. | 433/8 |
| 3,461,559 A | * | 8/1969 | Silverman et al. | 433/15 |
| 3,721,005 A | * | 3/1973 | Cohen | 433/16 |
| 3,946,488 A | * | 3/1976 | Miller et al. | 433/11 |
| 4,139,945 A | * | 2/1979 | DiGiulio | 433/16 |
| 4,186,488 A | * | 2/1980 | Wallshein | 433/8 |
| 4,243,387 A | * | 1/1981 | Prins | 433/16 |
| 4,487,581 A | * | 12/1984 | Adler | 433/16 |
| 4,597,739 A | * | 7/1986 | Rosenberg | 433/16 |
| 5,954,502 A | | 9/1999 | Tuenge et al. | |
| 7,306,458 B1 | * | 12/2007 | Lu | 433/16 |
| 7,431,586 B1 | | 10/2008 | Silverman | |

(Continued)

FOREIGN PATENT DOCUMENTS

WO   WO2008/119119 A1   10/2008
WO   WO2008/142690 A2   11/2008

OTHER PUBLICATIONS

Reinventing the Science of Braces (downloaded on May 7, 2012); http://www.suresmile.com.
Online Encyclopedia—Suresmile (downloaded on May 7, 2012); http://en.wikipedia.org/wiki/Suresmile.

(Continued)

*Primary Examiner* — Cris L Rodriguez
*Assistant Examiner* — Matthew Nelson
(74) *Attorney, Agent, or Firm* — Antoinette G. Giugliano; AGG Intellectual Property Law (57) ABSTRACT

This invention is an adjustable orthodontic bracket system which allows brackets to be adjusted for the particular angulations required for each individual tooth of any patient, while continuously attached to the tooth surface. The orthodontist manually adjusts the relationship of the bracket component with the frame and bracket base during treatment eliminating the necessity of repositioning bracket components due to erroneous positioning. The bracket component is positioned such that it can move completely in all directions to achieve the proper angulation for tooth repositioning. The base of the bracket component and the interior surface of the bracket compartment are textured to provide friction and secure the components once positioned for proper tooth movement. The exterior of the bracket component is also textured to provide more secure attachment to the surface of the tooth. This system will lead to lower treatment cost and quicker adjustments of the orthodontic bracket system.

11 Claims, 5 Drawing Sheets

(56) References Cited

U.S. PATENT DOCUMENTS

| | | | |
|---|---|---|---|
| 7,597,553 B2* | 10/2009 | Kimura | 433/16 |
| 7,819,660 B2* | 10/2010 | Cosse | 433/8 |
| 7,963,767 B2 | 6/2011 | Lewis et al. | |
| 8,038,438 B2 | 10/2011 | Ruiz Diaz et al. | |
| 8,459,988 B2* | 6/2013 | Dumas | 433/8 |
| 8,550,814 B1* | 10/2013 | Collins | 433/9 |
| 2005/0136369 A1* | 6/2005 | Rosenberg | 433/8 |
| 2007/0128571 A1* | 6/2007 | Kimura | 433/16 |
| 2007/0259302 A1* | 11/2007 | Jayawardena | 433/10 |
| 2008/0293005 A1 | 11/2008 | Rahlis et al. | |
| 2011/0300502 A1* | 12/2011 | Kishi | 433/10 |
| 2012/0225398 A1* | 9/2012 | Fallah | 433/8 |
| 2013/0078595 A1* | 3/2013 | Solano Reina et al. | 433/10 |

OTHER PUBLICATIONS

Online Encyclopedia—Self ligating braces (downloaded on Jun. 18, 2012); http://en.wikipedia.org/wiki/Self-ligating_braces.

Online Encyclopedia—Dental braces (downloaded on May 7, 2012); http://en.wikipedia.org/wiki/Dental_braces.

Dental Braces and Retainers: Types, Care, What to Expect (downloaded on May 7, 2012); http://www.webmd.com/oral-health/guide/braces-and-retainers.

Online Encyclopedia—Shape-memory alloy (downloaded on Jul. 2, 2013); http://en.wikipedia.org/wiki/Shape-memory_alloy.

Online Encyclopedia—Shape-memory polymer (downloaded on Jul. 2, 2013); http://en.wikipedia.org/wiki/Shape-memory_polymer.

* cited by examiner

DYNAMIC BRACKET SYSTEM

CROSS-REF. TO RELATED APPLICATIONS

None.

TECHNICAL FIELD

This invention relates to orthodontics, and more specifically to a system and method for customizing brackets for individual teeth.

BACKGROUND

Orthodontics is a specialty in dentistry that moves teeth within the jaw bone and straightens the teeth by moving them to the proper three-dimensional location. In orthodontics, brackets are pieces of metal with a slot that accepts a flexible or rigid metallic wire. Such brackets are conventionally bonded to the teeth on a base and serve as vehicles allowing the orthodontist to apply force to the tooth to move it across the wire to its proper location with the proper angulation.

The interaction of force, wires and brackets guides the three dimensional movement of the tooth. The force applied to the teeth, by the wire, forces the teeth to slowly alter their positions to align with the wire and therefore positioned correctly in three dimensions.

Conventional brackets have a fixed slot wherein the position of the slot relative to the tooth is fixed. Historically, brackets were the same for all teeth, regardless of patient individuality. Since every tooth has a unique three dimensional relationship with the rest of the teeth, the orthodontist was required to bend the wire that passed across the bracket slot in order to correct tooth angulation for each individual tooth.

In orthodontics, the angulation of the bracket slot in each dimension is described differently. The angulation of the bracket slot in the left-right direction is called 'tip' and the angulation of slot in the back-forward direction is called 'torque'. Each and every tooth, in a normal position, has a certain tip and torque. A modification was presented a few decades ago by which specific brackets were created for every tooth according to their average angulations so that when a straight wire was passed through the slot, the difference between the angle of the straight wire and the angle of the slot would force the tooth to track the wire and achieve the proper average angulation. However, the inaccuracies occurred when a bracket was not bonded to the proper location on the tooth, which led to an improper angulation of the tooth and ultimately a misaligned tooth.

Also, the presumed angulations are merely averages, based on estimates of average sizes and shapes of teeth. Each individual is different with varying morphology for their teeth. Whenever a patient's teeth do not fall within the normal range, the straight wire technique does not produce optimum tooth angulation and location. Commonly brackets are not always placed in the proper location on the tooth resulting in erroneous bracket positioning. In order to correct for such problems, a certain number of brackets are repositioned during the course of the treatment to address these inaccuracies and improper bracket placements. Repositioning is both time-consuming and expensive and oftentimes does not cure the improperly positioned bracket. The process of bracket repositioning involves a patient's office visit, removal of the old bracket, polishing the tooth surface, priming the surface and applying the new bracket to the surface. This process can take anything from 5 to 15 minutes per tooth, depending on the location of the bracket and the experience of the assistant.

A dynamic base for the bracket addresses these deficiencies by allowing the orthodontist to manually adjust the relationship of the slot with the base during the course of treatment. Recently, systems have been developed that incorporate movable brackets, however those systems have complicated designs and would be difficult to use in the practice of orthodontics.

In modern orthodontics, proper bracket placement determines the quality of orthodontic treatment as the practitioners have moved from bending wires to using brackets with pre-determined angulations of the slot relative to the bracket base. There are clear guidelines on how to place brackets accurately, so that with a straight wire that is not bent, the teeth will be automatically guided to their proper angulations.

With introduction of the dynamic bracket system, the need for repositioning brackets due to erroneous positioning will be eliminated. This change will lead to lower treatment cost by decreasing the amount of time the patient spends at the clinic (less time away from work or school) and decreasing patient treatment time chair side. In addition, the quality of care delivered to the patient from the orthodontist is greatly improved.

SUMMARY OF THE INVENTION

The present system is designed to equip the practitioner with the ability to conveniently modify the position, tip and torque of the bracket slot component during the course of treatment, without having to remove and rebond the bracket, using the dynamic bracket system. The dynamic bracket system will increase efficiency and quality of patient care. A dynamic bracket system consists of a frame, bracket slot component, stationary cover and a moving cover. The frame, with its textured bottom side, is bonded to the tooth surface with an adhesive material commonly used in orthodontics. The bracket slot component includes a base, a stem and the top portion of the bracket, which includes an upper arm, a slot, and a lower arm.

The bracket system uses friction to secure the slot component after it is repositioned. Within the bracket system, the stem, immediately below the top portion of the bracket, is positioned within the bracket compartment opening, between the junction of the moving cover and stationary cover. The bracket base is secured by vertical pressure from the joining of the moving cover and stationary cover within the frame. The base of the bracket slot component, below the stem, rests above the textured interior of the bracket frame. The textured interior surface ensures that the bracket component does not move freely within the space created between bracket frame and the covers. The diameter of the bracket stem is smaller than the opening created by the covers such that the bracket stem fits within the opening. The base of the bracket slot component is wider than the stem yet narrower than the frame.

The dynamic bracket system also includes a stationary cover and a moving cover which slide into position within the bracket frame along guiding grooves in the interior side walls of the bracket frame. The guiding groove is an indention that runs along the top interior edge of the frame. The ends of the stationary cover and moving cover are tapered to allow sliding of the moving cover over the stationary cover in the guiding groove. The horizontal force on the covers as the covers move towards the end of the grooves, sliding friction of the covers over one another, as well as vertical pressure on the base of the bracket combine to limit the movement of the covers.

Each cover has depressions at the exterior edge of the cover, which lock onto projections along the guiding groove of the frame. In this embodiment, the stationary cover and moving cover both have irregularly shaped interior edges. When the stationary and moving covers are in position within the bracket frame, an opening to the bracket slot compartment is created at the junction of the interior edge of the two covers. During initial assembly of the bracket, first, the stationary cover is guided into position within the bracket frame, along the guiding grooves. The stationary cover is locked into place when the depression on the stationary cover connects with the projection along guiding groove.

The bracket slot component is inserted into the space between the cover and the frame so that the base of the slot component lies beneath the cover and the rest of the slot component lies above it. Finally, the moving cover is guided into position within the bracket frame until the depressions connect with the projections of the guiding groove. The bracket slot component is secured between the frame and the covers by the secure connection between the stationary cover and the moving cover. The covers are locked together by a locking mechanism such as ball and socket, key and key hole or force of friction. The guiding grooves are slightly wider than the width of the covers so that when the two covers come together, the stationary cover is pushed down as the moving cover is wedged between the guiding groove and the moving cover. Without the slightly wider guiding grooves, a positive pressure or force of friction would not be created to secure the covers.

This design allows for the bracket slot component to be adjusted within the confines defined by the stationary cover and moving cover when the moving cover is in the 'open' configuration and not fixed in place. The bracket slot component locks in place when the moving cover is in the 'lock' configuration. The slot component is able to rotate 360 degrees as well as move within the range defined by the difference in radius of the stem and the opening to the bracket compartment (also referred to as the inner borders of the covers. The frame's exterior, or tooth-side surface is textured to increase bond strength. The tooth-side surface of the bracket frame has adaptive curves associated with the morphology of tooth surface. The base of the stem and the base-side of the frame have micro-depressions to prevent sliding of the slot when the moving cover is in lock position. This bracket system uses friction as a means to prevent alteration of position of bracket slot relative to the frame.

The two covers have a locking mechanism when they meet that prevents the moving cover from opening unless subjected to horizontal force applied through a regular orthodontic plier to its opening ledge. When the two cover extensions meet, a positive downward pressure or force of friction is applied on the base of the slot component, locking it in place. This increased positive pressure is created as the sloped surface of the moving cover extension slides above the sloped surface of the stationary cover extension. The moving cover is held in place by the guiding grooves or narrow cut outs made in the inner surface of the walls of the base frame, allowing it to move back and forth in the horizontal direction. When the stationary cover is positioned in the frame wall's guiding groove, it will lock in place when pushed to the edge of the frame and the opposing socket in the stationary cover. The moving cover is locked in place when engaged with the stationary cover. The stationary cover and the moving cover are secured when the depressions on these covers are positioned within the projections in the guiding groove, at the exterior edge of the frame. The frame wall surrounds the bracket frame except the feeding wall where it allows for the base of the bracket compartment to slide underneath the covers. The moving cover has a notch close to the edge on the feeding side of the frame that prevents it from coming loose when the moving cover is open unless subjected to sufficient force from a human hand using a dental plier or other tool. When subjected to sufficient force, practitioner can replace the moving cover in cases where breakage happens or the practitioner is required to modify the slot configuration for any reason, whether it is damaged or a different torque number is required.

OBJECTS OF THE INVENTION

An object of the present invention is to provide a bracket system quickly tailored to each individual tooth in a patient's mouth, during treatment.

Another object of the present invention is to provide a faster system for bracket repositioning that does not involve removing the entire bracket system for each tooth.

Another object of the present invention is to decrease the amount of time a patient spends at the orthodontist's office.

Another object of the present invention is to reduce the orthodontist's time spent on each patient and to reduce amount of work required for each patient.

Another object of the present invention is to provide a system for bracket repositioning wherein the brackets can be repositioned to account for variable angulations and positions in a matter of seconds.

Another object of the present invention is to provide a bracket system such that its slot position, tip and torque measurements can be modified while still attached to the tooth surface.

DETAILED DESCRIPTION OF DRAWINGS

Figure 1:
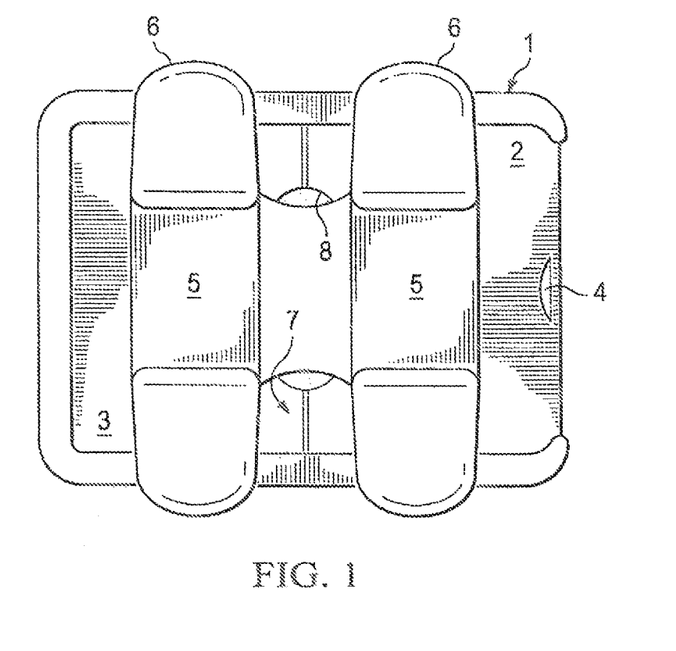
FIG. 1 is a front view of the dynamic bracket system
Ref. 1 is the bracket system frame
Ref. 2 is the moving cover
Ref. 3 is the stationary cover
Ref. 4 is the releasing notch.
Ref. 5 is the bracket wire slot
Ref. 6 is a bracket slot component
Ref. 7 is the junction between the moving and stationary covers
Ref. 8 is the opening to the bracket component

FIG. 1 is a front view of the dynamic bracket system. The dynamic bracket system is composed of a bracket system frame (1) which is connected to the tooth surface (9). The interior of the frame has grooves or guiding lines (17) for the insertion of the stationary cover and moving cover. The moving cover (2) is inserted after the stationary cover (3) into the frame such that the covers connect at a junction (7). The connected covers exert a vertical pressure on the bracket base (10) that helps secure the base inside the bracket compartment (16). The moving cover (2) has a releasing notch (4) into which an orthodontic plier or tool can be inserted in order to release the moving cover from the frame (1). Once the stationary cover (3) is in place within the frame, the bracket slot component (6) is inserted followed by another bracket slot component (6). Each bracket slot component has a bracket wire slot (5) for the insertion of a guiding wire into the bracket system. The interior edges of both the stationary cover and the moving cover contain a cutout section such that an opening to the bracket compartment (8) is created where the bracket slot component (6) will be inserted within the bracket system.

Figure 2:
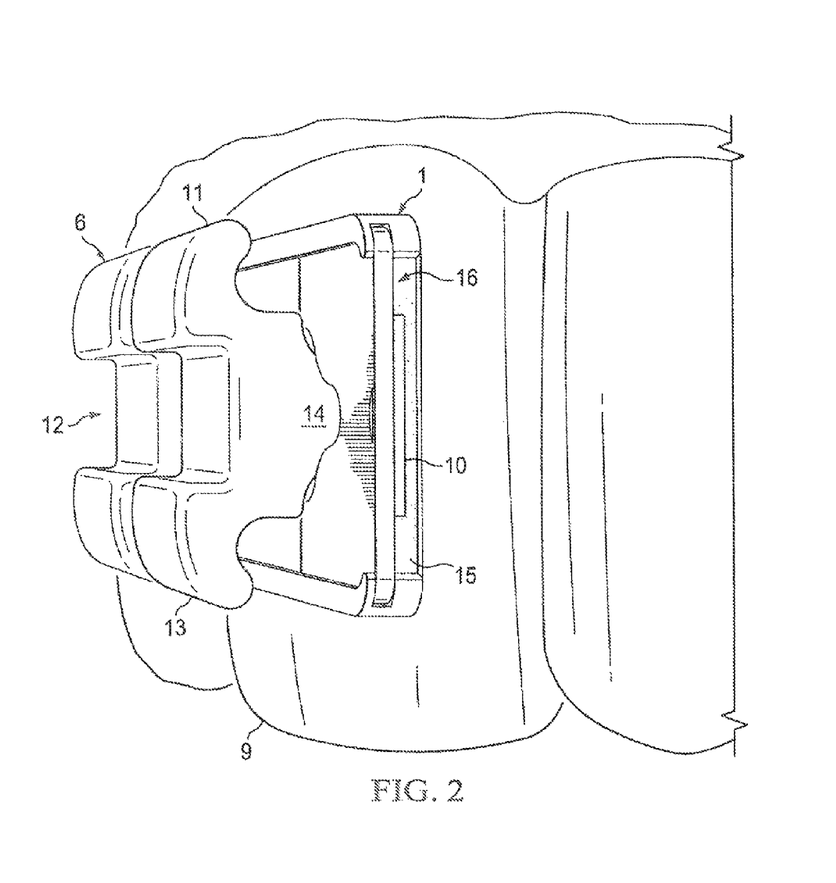
FIG. 2 is a side view of the dynamic bracket system
Ref. 1 is the bracket system frame
Ref. 6 is the bracket slot component
Ref. 9 is the tooth surface
Ref. 10 is the bracket base
Ref. 11 is the upper arm of the bracket slot component
Ref. 12 is the wire slot of the bracket slot component
Ref. 13 is the lower arm of the bracket slot component
Ref. 14 is the bracket stem
Ref. 16 is the bracket slot compartment

FIG. 2 is a side view of the dynamic bracket system. The bracket system is attached to the front surface of the user's tooth (9). The bracket slot component (6) is composed of an upper arm (11), a wire slot (12), a lower arm (13), a stem (14) and a base (10). The bracket slot component (6) is inserted into the frame (1) between the stationary cover and moving cover. The bracket base (10) of the bracket slot component rests beneath the stationary and moving covers in the bracket slot compartment (16), where the bracket base is secured by vertical pressure from the covers. The interior surface of the bracket slot compartment is textured (15) to prevent movement of the bracket slot component (6). The bracket stem (14) is inside the opening (8) for the bracket slot compartment (16). The opening (8) is created by the joining of the edges of the stationary cover and moving cover. Each cover has an irregularly shaped interior edge, which creates an opening to the compartment (8) to allow for the insertion of the bracket stem between the joined covers.

Figure 3:
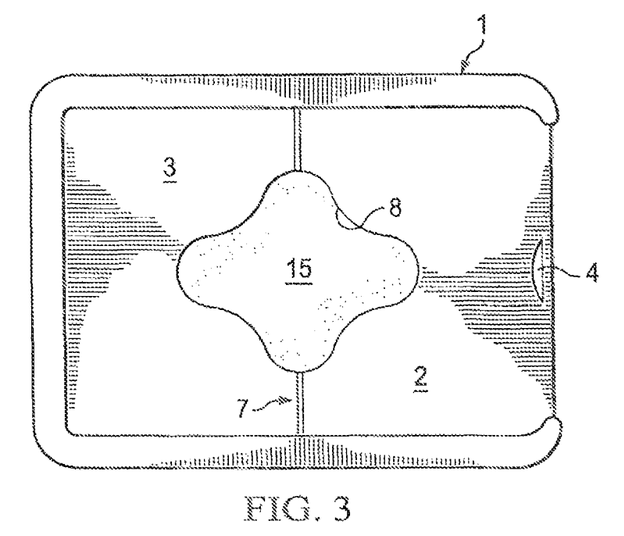
FIG. 3 is a front view of the bracket slot compartment opening created by the joining of the stationary and moving covers
Ref. 1 is the bracket system frame
Ref. 2 is the moving cover
Ref. 3 is the stationary cover
Ref. 4 is the releasing notch
Ref. 7 is the junction between the moving and stationary covers
Ref. 8 is the opening for the bracket slot compartment

FIG. 3 is a front view of the bracket slot compartment opening created by the joining of the stationary and moving covers. The stationary and moving covers each contain an irregularly shaped interior edge that creates an opening (8) for the bracket slot compartment when the covers are aligned. The stationary cover (3) is inserted into the bracket system frame (1) along the guiding grooves (17). Then the moving cover (2) is also inserted along the guiding grooves (17) until its sloped edge meets the sloped edge of the stationary cover (3) at the junction point (7). The outer edge of the moving cover (4) has a releasing notch (4) that assists in the removal of the moving cover. Pressure applied to the releasing notch with a dental tool will release the moving cover from its position. The dental tool can be any types of the following: cutter, explorer, plier, stripper, or scaler. The opening (8) to the bracket slot component is created by the joining of the stationary and moving covers at their interior edges.

Figure 4:
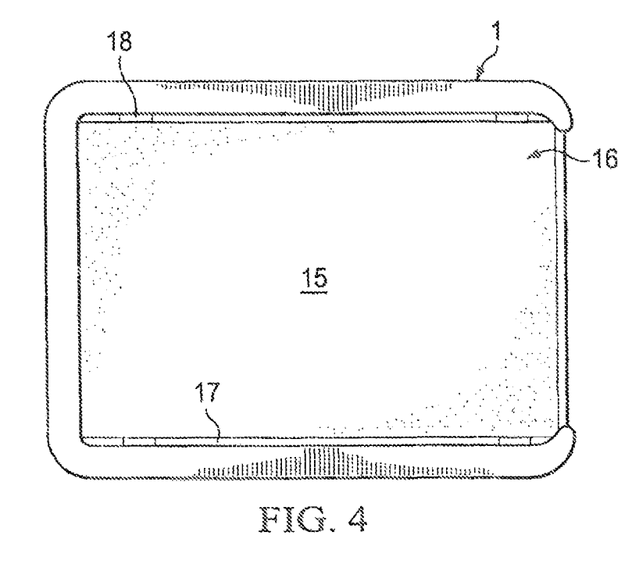
FIG. 4 is a front view of the bracket slot compartment without covers
Ref. 1 is the bracket frame
Ref. 15 is the textured surface of the interior of the bracket slot compartment
Ref. 16 is the bracket compartment
Ref. 17 is the guiding grooves within the interior of the frame

FIG. 4 is a front view of the bracket slot compartment (16) without the stationary cover or moving cover. The components of the bracket system are assembled within the bracket frame (1). The interior edges of the frame have guiding grooves (17) that the stationary and moving covers glide along as the covers are inserted into the frame. The interior surface of the bracket compartment is textured (15) to prevent movement of the bracket base (10) within the compartment (16).

Figure 5:
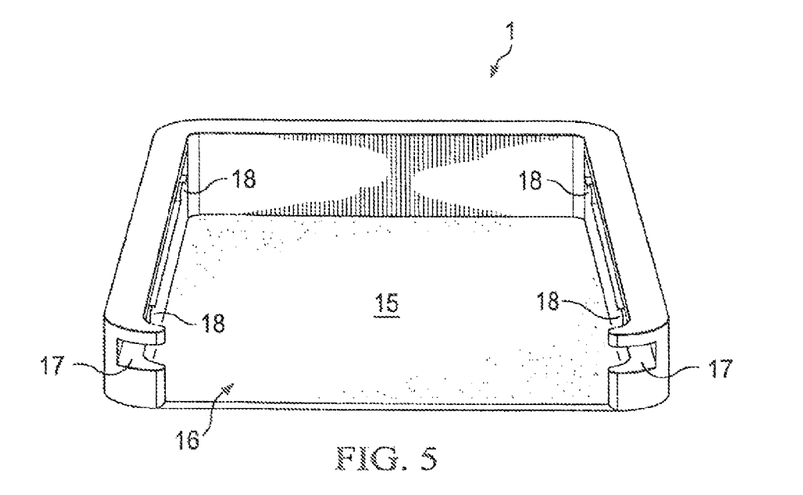
FIG. 5 is a side view of the bracket slot compartment without covers
Ref. 1 is the bracket frame
Ref. 15 is the textured surface of the interior of the bracket slot compartment
Ref. 16 is the bracket compartment
Ref. 17 is the guiding grooves within the interior of the frame
Ref. 18 is a projection along the guiding groove

FIG. 5 is a side view of the bracket slot compartment (16) without the stationary cover or moving cover. The components of the bracket system are assembled within the bracket frame (1). The interior edges of the frame (1) have guiding grooves (17) that the stationary and moving covers glide along as the covers are inserted into the frame (1). There are a number of projections (18), along the surface of the guiding grooves (17) that lock with the depressions (19) on the moving and stationary covers to secure the covers to the frame (1). The connection between the projections (18) and the depressions (19) also exerts vertical pressure on the bracket base (10) within the bracket compartment (16). The interior surface of the bracket compartment (16) is textured (15) to prevent movement of the bracket base within the compartment (16).

Figure 6:
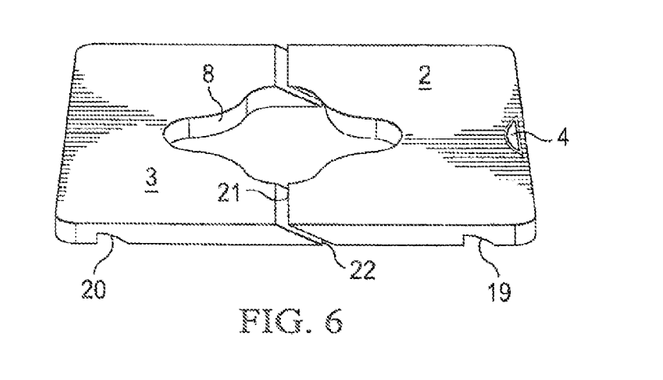
FIG. 6 is a bottom view of the stationary cover and moving cover in an unlocked position
Ref. 2 is the moving cover
Ref. 3 is the stationary cover
Ref. 4 is the releasing notch
Ref. 8 is the opening for the bracket slot compartment created by the joining of the moving and stationary covers
Ref. 19 is the securing depression on the moving cover
Ref. 20 is the securing depression on the stationary cover
Ref. 21 is the connecting edge of the moving cover
Ref. 22 is the connecting edge of the stationary cover

FIG. 6 is a bottom view of the stationary cover and moving cover in an unlocked position. The moving cover (2) and the stationary cover (3) both have connecting edges (21, 22) that lock together at the junction. In addition, the moving cover (2) and the stationary cover (3) both have cutout sections on the interior edges of the covers. When the moving cover and the stationary cover are locked or joined, a closed off round opening (8) is created. The bracket component will be positioned within this opening (8) to the bracket slot compartment (16) when the bracket system is fully assembled. The moving cover has dual securing depressions (19) at its exterior edges that serve to secure the moving cover (2) and prevent the cover from falling out of the frame (1). These depressions (19) connect with projections (18) along the guiding groove (17) to secure the cover in the frame. The stationary cover also has dual securing depressions (20) at its outer edges that serve to secure the stationary cover (3) and prevent the cover from falling out of the frame. The securing depressions on the bottom side of the covers protrude and prevent the covers from sliding out of position. These depressions (20) connect with projections (18) along the guiding groove (17) to secure the cover in the frame (1). There is also a releasing notch (4) that unlocks the cover once an orthodontic plier is inserted in the latch with sufficient force from a hand and dental tool.

Figure 7:
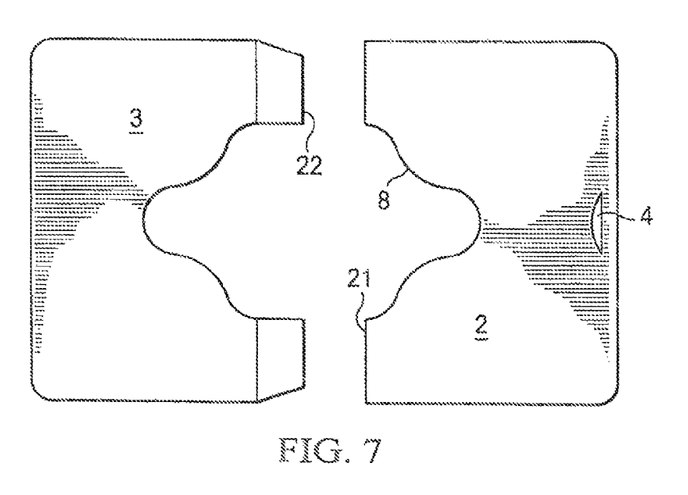
FIG. 7 is a close up of front view of the covers in an unlocked position
Ref. 2 is the moving cover
Ref. 3 is the stationary cover
Ref. 4 is the releasing notch
Ref. 8 is the opening for the bracket slot compartment created by the joining of the moving and stationary covers
Ref. 21 is the connecting edge of the moving cover
Ref. 22 is the connecting edge of the stationary cover

FIG. 7 is a close-up front view of the covers in an unlocked position. The moving cover (2) and the stationary cover (3) both have connecting edges (21, 22) that lock together at the junction and cutout sections on the interior edges of both covers. When the moving cover and the stationary cover are locked or joined, a closed off round opening (8) is created. The moving cover has dual depressions (19) at its outer edges that serve to secure the moving cover and prevent the cover from falling out of the frame. The stationary cover also has dual securing depressions (20) at its outer edges that serve to secure the stationary cover (3) and prevent the cover from falling out of the frame. There is also a releasing notch (4) that unlocks the cover once an orthodontic plier is inserted in the latch with sufficient force from a hand and dental tool.

Figure 8:
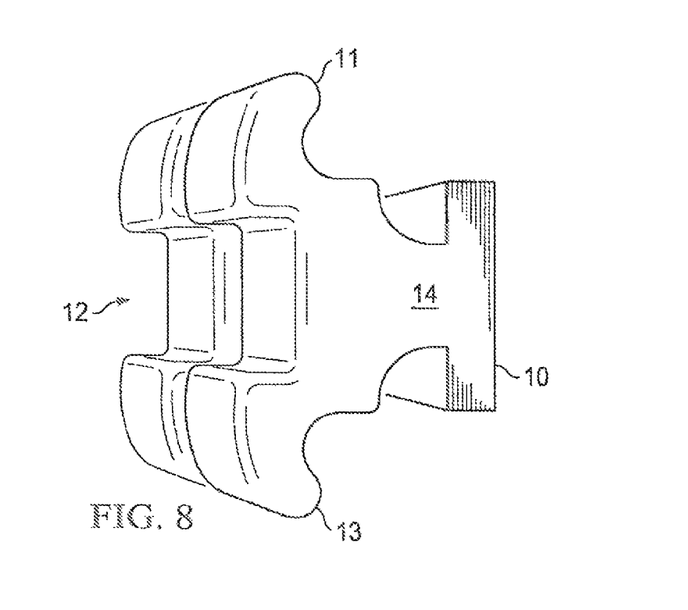
FIG. 8 is a side view of the bracket slot component
Ref. 10 is the base of the bracket
Ref. 11 is upper arm of the bracket slot component
Ref. 12 is the slot of the bracket where the orthodontic wire is inserted
Ref. 13 is the lower arm of the bracket component
Ref. 14 is the stem of the bracket

FIG. 8 is a side view of the bracket component. The bracket slot component is made of an upper arm (11) and lower arm (12) with a slot (13) between the arms wherein an orthodontic wire would be inserted to aid in the movement of teeth. Beneath the slot (13), lies the stein (14) of the bracket slot component. The stem is of a considerably smaller diameter than the distance between the upper and lower arms of the bracket component. Beneath the stem, lies the base of the bracket (10) which is of a length larger than the stem yet smaller than the distance between the upper and lower arms. The stem (14) of the bracket slot component is inserted through the bracket compartment opening (8) and the base (10) of the bracket slot component rests against the textured interior surface (15) of the bracket compartment in the bracket frame (1).

What is claimed:

1. A system of adjustable brackets for use with orthodontic braces comprising:
   a. a frame;
   b. a bracket; wherein the bracket comprises a bracket top, a bracket stem, and a bracket base; wherein the bracket top comprises an upper arm positioned above a slot and a lower arm positioned below the slot, wherein the slot is positioned between the upper arm and the lower arm, wherein the bracket top is affixed to the bracket stem, wherein the bracket stem is attached to the bracket base; and
   c. a number of frame covers comprising at least a first frame cover and a second frame cover;

wherein the bracket is positioned between the first frame cover and the second frame cover within an opening formed between interior edges of the first frame cover and the second frame cover, wherein said first frame cover contains at least one depression at an exterior edge of said first frame cover, wherein said second frame cover contains at least one depression at an exterior edge of said second frame cover, such that said depressions secure said first frame cover and said second frame cover within said frame along an indentation, wherein said indentation is along a top interior edge of said frame.

2. The system of claim 1, wherein said opening accommodates said bracket such that said interior edge of said first frame cover is positioned adjacent to a first half of said bracket stem, wherein said interior edge of said second frame cover is positioned adjacent to a second half of said bracket stem, such that said bracket is secured within said opening.

3. The system of claim 2, wherein the interior edge of said first frame cover and the interior edge of said second frame cover connect by at least one junction point such that an opening is formed when said interior edge of said first frame cover and said interior edge of said second frame cover are aligned at said junction point.

4. The system of claim 3, wherein said second frame cover has a locking mechanism such that said second frame cover is securely attached to said first frame cover within said frame.

5. The system of claim 4, wherein said locking mechanism type is selected from the group consisting of ball and socket, key and key hole, and force of friction.

6. The system of claim 1, wherein said indentation contains at least one projection to accommodate said at least one depression of said first frame cover, wherein said indentation contains at least one projection to accommodate said at least one depression of said second frame cover, such that said first frame cover and said second frame cover are secured within said indentation of said frame.

7. The system of claim 6, wherein said second frame cover contains a notch at about the midpoint of said exterior edge, wherein said second frame cover is released from said frame upon the application of sufficient force to said notch of said second frame cover, wherein said sufficient force is force of an amount consistent with the force applied by a human hand or dental tool.

8. The system of claim 1, wherein said frame is composed of three walls, of about the same height, and an open fourth side, wherein said frame contains an indentation along a top interior edge of said frame.

9. The system of claim 8, wherein an interior bottom side of said frame is textured such that a surface of said interior bottom side is not smooth and wherein an exterior bottom side of said frame is textured such that a surface of said exterior bottom side is not smooth.

10. The system of claim 9, wherein an exterior bottom surface of said bracket base is textured.

11. The system of claim 8, wherein said first frame cover and said second frame cover insert into said frame along said indentation.

* * * * *